US005591897A

United States Patent [19]
Nakamura et al.

[11] Patent Number: 5,591,897
[45] Date of Patent: Jan. 7, 1997

[54] APPARATUS FOR AND METHOD OF MEASURING GAS ABSORBING CHARACTERISTICS

[75] Inventors: Hiroshi Nakamura, Neyagawa; Shin Fujitani, Hirakata; Yumiko Nakamura, Moriguchi; Takahiro Yonesaki, Gunma; Koichi Nishimura, Suita; Teruhiko Imoto, Kadoma; Ikuo Yonezu, Hirakata, all of Japan

[73] Assignee: Sanyo Electric Co., Ltd., Osaka, Japan

[21] Appl. No.: 466,045

[22] Filed: Jun. 6, 1995

[30] Foreign Application Priority Data

Jun. 24, 1994 [JP] Japan .................................. 6-143343

[51] Int. Cl.$^6$ .................................................. G01N 15/08
[52] U.S. Cl. .................................................. 73/38; 73/865.5
[58] Field of Search ........................ 73/19.07, 38, 865.5, 73/49.2

[56] References Cited

U.S. PATENT DOCUMENTS

| | | | |
|---|---|---|---|
| 3,059,478 | 10/1962 | Coggeshall et al. | 73/38 |
| 3,732,736 | 5/1973 | Glaude et al. | 73/865.5 |
| 3,850,040 | 11/1974 | Orr, Jr. et al. | 73/38 X |
| 4,661,415 | 4/1987 | Ebato et al. | 428/570 |
| 4,762,010 | 8/1988 | Borghard et al. | 73/38 X |
| 4,972,730 | 11/1990 | Camp et al. | 73/865.5 |
| 5,058,442 | 10/1991 | Yamanaka et al. | 73/865.5 |
| 5,239,482 | 8/1993 | Ajot et al. | 73/38 X |
| 5,360,743 | 11/1994 | Lowell | 73/38 X |

FOREIGN PATENT DOCUMENTS 0538622  2/1994  European Pat. Off. .

OTHER PUBLICATIONS

Miyamoto M. et al., "Reaction Kinetics of LaNi$_5$", *Journal of the Less Common–Metals*, vol. 89, 1983, pp. 111–116.

Hwang, C. et al., "Diffusion of Hydrogen in Amorphous Cu$_{45}$Ti$_{55}$ Ribbon", *Journal of the Less–Common Metals*, vol. 89, 1983, pp. 215–222.

*Primary Examiner*—Michael Brock
*Attorney, Agent, or Firm*—Armstrong, Westerman, Hattori, McLeland & Naughton

[57] ABSTRACT

The invention relates to an apparatus for measuring the gas absorbing and/or desorbing characteristics of a substance having a property to absorb a gas. The apparatus comprises a sample container for containing the substance, a gas storage connected to the sample container for storing the gas until a predetermined pressure is reached, a gas supply source for supplying the gas to the gas storage, a first valve provided on a line connecting the gas supply source to the gas storage, a second valve provided on the line between the first valve and the gas storage, and a third valve provided on a gas discharge line connected to the line between the first and second valves, the first to third valves being each a two-position valve having an open position and a closed position, the valves defining a region thereby surrounded and serving as a preliminary storage for temporarily holding the gas when the gas is supplied or discharged. The substance having the gas absorbing property is, for example, a hydrogen absorbing alloy, and the gas is hydrogen.

7 Claims, 18 Drawing Sheets

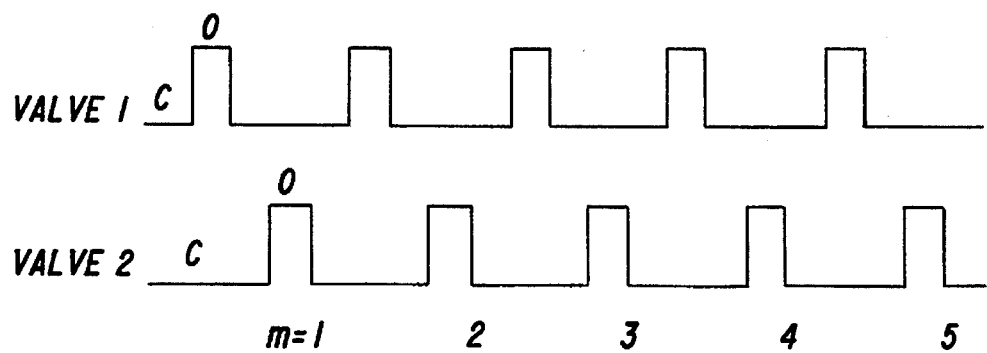
FIG.3   O : OPEN STATE   C : CLOSED STATE
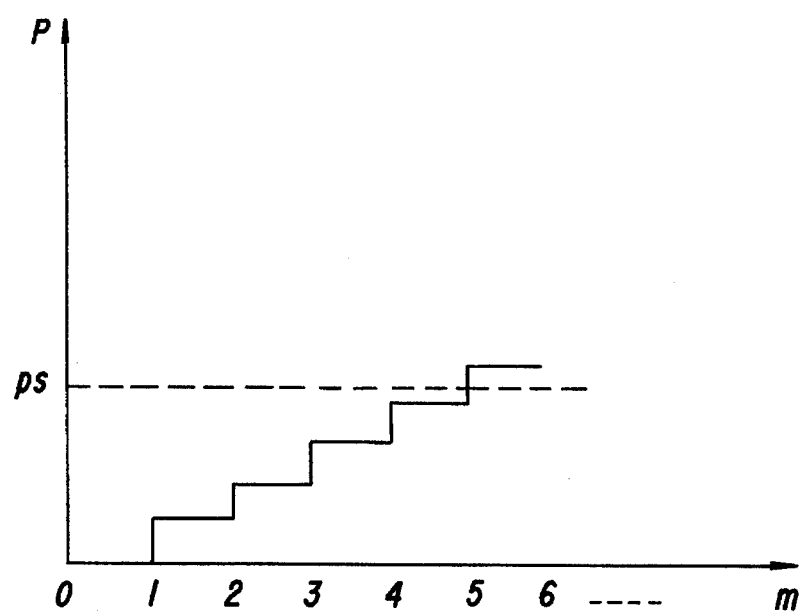
FIG.4

FIG.5
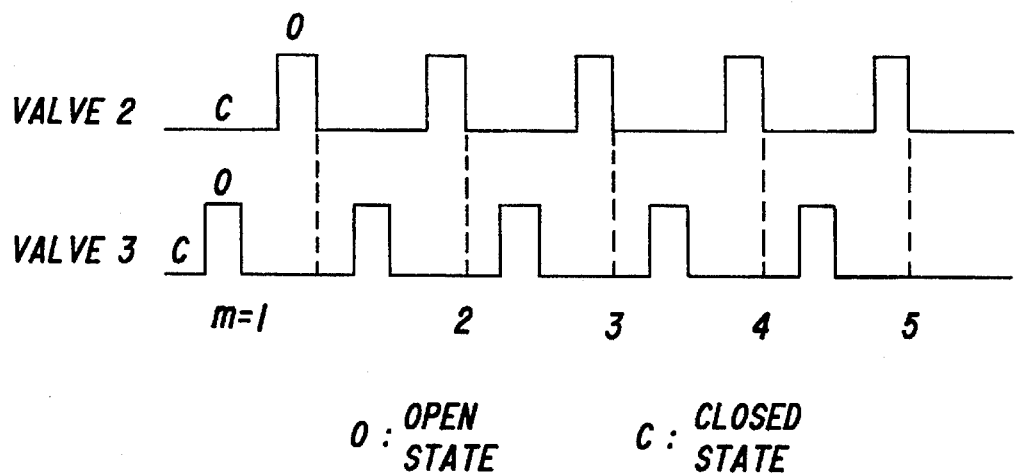
O : OPEN STATE     C : CLOSED STATE
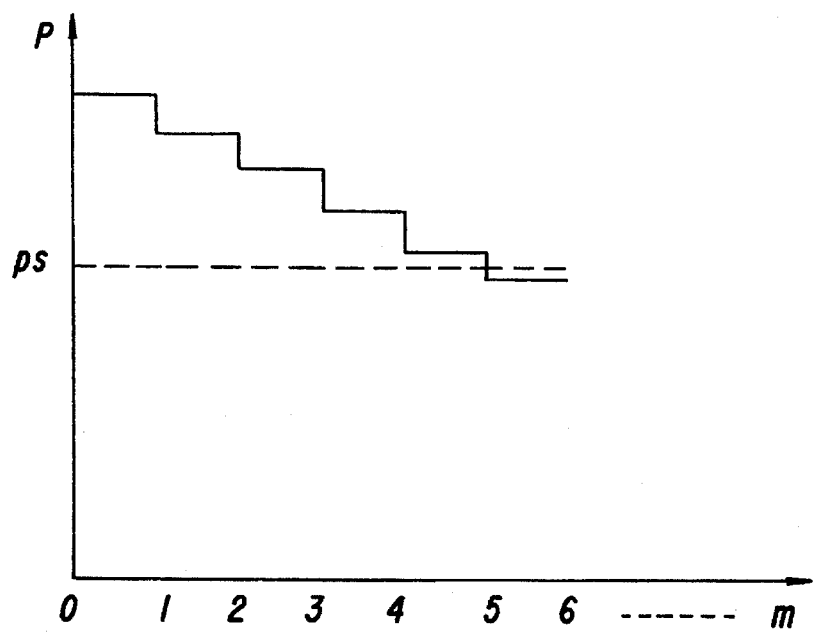
FIG.6

FIG. 10

| | SAMPLE HOLDER SETTING THERMOSTAT TEMPERATURE SETTING | EVACUATION | INTRODUCTION OF SPECIFIED GAS | ABSORPTION REACTION |
|---|---|---|---|---|
| 1 (28) | C | | | |
| 2 (29) | C | | | |
| 3 (30) | C | | | |
| 4 (31) | C | | | |
| 36 (32) | C | C | C ↔ O | |
| 37 (33) | C | C | O ↔ C | |
| 42 | C | C | c | c |
| 48 | C | O | c | c |
| 49 | C | O | O | O |
| 34 | C | O | c | c |
| 35 | C | C | O | O |
| 51 | C | O | c | c |

C: CLOSED STATE  O: OPEN STATE  c ↔ o, o ↔ c: REPETITION OF C AND O

FIG.14

| | SAMPLE CONTAINER SETTING TEMPERATURE SETTING | EVACUATION | APPLICATION OF SPECIFIED PRESSURE DIFFERENCE | ABSORPTION REACTION |
|---|---|---|---|---|
| 1 (28) | C | C | C ↔ O | C |
| 2 (29) | C | C | O ↔ C | C |
| 3 (30) | C | C | C | C |
| 4 (31) | C | O | C | C |
| 36 (32) | C | C | C | O |
| 37 (33) | C | O | C | C |
| 42 | C | O | O | C |
| 48 | C | O | C | C |
| 49 | C | C | O | O |
| 34 | C | C | C | C |
| 35 | C | O | C | C |
| 51 | C | O | O | O |

C:CLOSED STATE   O:OPEN STATE   C ↔ O, O ↔ C: REPETITION OF C AND O

FIG.18

| | SAMPLE CONTAINER SETTING TEMPERATURE SETTING | DISCHARGING GAS WITH PRESSURE DIFFERENCE | DESORPTION REACTION |
|---|---|---|---|
| 1 (28) | C | C | C |
| 2 (29) | C | C | C |
| 3 (30) | C | O | C |
| 4 (31) | C | C | O |
| 36 (32) | C | C | C |
| 37 (33) | C | O | C |
| 42 | C | C | C |
| 48 | C | C | O |
| 49 | C | C | C |
| 34 | C | O | O |
| 35 | C | C | C |
| 51 | C | O | O |

C: CLOSED STATE  O: OPEN STATE  0,0  C: REPETITION OF C AND O $MmNi_{4.3}Mn_{0.4}Al_{0.3}$ AT 40.0°C

APPARATUS FOR AND METHOD OF MEASURING GAS ABSORBING CHARACTERISTICS

FIELD OF THE INVENTION

The present invention relates to apparatus adapted to cause a substance capable of absorbing and desorbing a gas to absorb or desorb the gas for measuring the absorbing or desorbing characteristics thereof, and more particularly to an apparatus for measuring the hydrogen absorbing or desorbing characteristics of hydrogen absorbing alloys.

BACKGROUND OF THE INVENTION

In recent years, attention has been directed to hydrogen absorbing alloys for the negative electrodes of alkali batteries and as hydrogen storage materials. Such hydrogen absorbing alloys are prepared by alloying a mixture of a rare-earth metal and a transition metal in a specified ratio, and typical of these alloys are, for example, $LaNi_5$, $MmNi_2Co_3$ (wherein Mm is a misch metal), etc.

In designing various devices, it is important to measure the hydrogen absorbing/desorbing characteristics of hydrogen absorbing alloys. These characteristics are used for setting the amount of hydrogen to be retained, pressure resistance, etc., are data indispensable to the provision of safety devices and are utilized also for improving the alloy when required.

The hydrogen absorbing/desorbing characteristics are represented basically by a pressure-composition isotherm (PCT) diagram. As shown in FIG. 21, the diagram represents the relationship between the pressure (ordinate) and the amount of hydrogen absorption (abscissa) under a specified temperature condition.

FIG. 20 shows a Sieverts' device conventionally used for measuring the data required for preparing a PCT diagram.

The Sieverts' device has a sample container 161 packed with a sample 162 of the hydrogen absorbing alloy to be checked for characteristics, and a gas storage container 164 connected to the container 161 via a manual valve 163. A hydrogen supply source 166 is connected to the gas storage container 164 by a hydrogen supply pipe provided with a manual valve 165. The gas storage container 164 is connected to a hydrogen discharge pipe via a manual valve 167 and further to a vacuum pump 168. With the valves 165 and 167 closed, the pressure and temperature of hydrogen gas are measured respectively by a pressure sensor 169 and a temperature sensor which is provided on the storage container 164.

The hydrogen absorbing characteristics are measured by this device by the following procedure.

First, hydrogen gas of specified pressure is supplied from the gas storage container 164 to the sample container 161 at a specified temperature. At this time, the hydrogen content of the sample alloy is measured to calculate the amount of absorbed hydrogen (wt. % or atomic ratio). The amount of absorbed hydrogen can be calculated, for example, from the pressure difference resulting from the introduction of hydrogen and the internal volume of the system using an equation of state of the gas. The amount of absorbed hydrogen and the hydrogen gas pressure value thus obtained are plotted on a PCT diagram (o mark in FIG. 21).

Next, hydrogen gas of slightly increased pressure is supplied to the sample container, similarly followed by measurement of the hydrogen content of the sample and calculation of the amount of absorbed hydrogen. The value of hydrogen gas pressure and the amount of absorbed hydrogen are plotted on the PCT diagram.

In this way, the pressure of the hydrogen gas to be supplied is increased stepwise, the hydrogen content of the sample alloy is measured every time, and the pressure value and the amount of absorbed hydrogen are plotted. For the determination of hydrogen desorbing characteristics, the pressure is conversely decreased stepwise.

For preparing the PCT diagram from the measurement data, the items of data necessary for the alloy sample are about 20 points in the direction of absorption (pressure increase direction) and about 20 points in the direction of desorption (pressure decrease direction), i.e., about 40 points in total. When the PCT diagram is prepared at each of different specified temperatures, 40 points multiplied by the number of different temperatures is the total number of measurements.

The hydrogen gas pressure is set by adjusting the degree of opening of the manual valve 165. When the hydrogen gas pressure is to be set at a value of about 0.01 to about 0.5 MPa, it is usually necessary to vary the pressure within the range of about 0.01 to about 0.1 MPa. However, the pressure of hydrogen gas cylinders serving as the hydrogen supply source is 12 to 15 MPa when the cylinder is filled up, and the pressure is as high as about 5 to about 6 MPa even when reduced by a regulator. It is therefore difficult to finely adjust the amount of hydrogen gas to be set.

Needle valves are generally used as the valves of the device. These valves wear if opened and closed every time the measurement is made, whereas since hydrogen molecules are extremely small, the wear, if slight, permits a leak and is objectionable.

FIG. 22 shows a device proposed to reduce the opening and closing frequency of the manual valve 165 and effect automated measurement. This device has a resistance pipe 170 and an inlet valve 171 of the two-position change-over type between the manual valve 165 and the gas storage container 164. An outlet valve 172 of the two-position change-over type and a resistance pipe 173 are arranged also between the gas storage container 164 and the vacuum pump 168. The resistance pipe 173 is provided with a bypass line which has a bypass valve 174.

With this device, when the gas is introduced, the valves 165, 171 are opened, the valves 172, 163 are closed, and the state of pressure is monitored at all times by the pressure sensor 169. Upon the gas pressure exceeding a set value, the valve 171 is closed and the valve 163 is opened. When the gas is discharged, the valves 163, 171 are closed, the valves 172, 174 are opened, and the state of pressure is always monitored by the pressure sensor 169 as in the case of introduction of the gas. Upon the gas pressure dropping below a set value, the valve 172 is closed, and the valve 163 is opened. Thus, feedback control is resorted to for closing the valves 171, 172 after the set pressure is reached and therefore requires pressure monitoring means of high time resolution or a high-speed data logger. Delay in response leads to a great deviation from the set value.

Since the manual valve 165 is always left open during the introduction and discharge of the gas, the valve is free of the objectionable wear due to repeated opening and closing unlike the device of FIG. 20, but the flow rate of the gas is adjusted by varying the opening degree of valve and is accordingly difficult to adjust finely.

An object of the present invention which has overcome the foregoing problems is to provide a measuring apparatus and a measuring method which readily permit fine adjustment of set pressure of the gas to be supplied or discharged without necessitating a high-speed data logger or the like.

SUMMARY OF THE INVENTION

The present invention relates to an apparatus for measuring the gas absorbing and/or desorbing characteristics of a substance having a property to absorb a gas. The apparatus comprises a sample container for containing the substance, a gas storage connected to the sample container for storing the gas until a predetermined pressure is reached, a gas supply source for supplying the gas to the gas storage, a first valve provided on a line connecting the gas supply source to the gas storage, a second valve provided on the line between the first valve and the gas storage, and a third valve provided on a gas discharge line connected to the line between the first valve and the second valve, the first, second and third valves being each a two-position valve having an open position and a closed position, the valves defining a region thereby surrounded and serving as a preliminary storage for temporarily holding the gas when the gas is supplied or discharged.

Preferably, the gas storage is provided with a gas holder for adjusting the amount of gas to be stored in the gas storage.

When the gas is supplied, the first valve and the second valve are alternately opened and closed to intermittently supply the gas stored in the preliminary storage to the gas storage and pressurize the gas storage stepwise until the predetermined pressure is reached. The gas stored in the gas storage to the predetermined pressure is supplied to the sample container at a time.

When the gas is discharged, the second valve and the third valve are alternately opened and closed to temporarily hold the gas of the gas storage in the preliminary storage, thereafter discharge the gas to a gas discharge portion intermittently and relieve the gas storage of pressure stepwise to a predetermined pressure.

BRIEF DESCRIPTION OF THE DRAWINGS

FIG. 3 is a diagram for illustrating a control sequence of opening and closing a first valve and a second valve alternately;

FIG. 4 is a graph showing the relationship between the number m of times the first valve and the second valve are opened and closed and the pressure P of a hydrogen storage;

FIG. 5 is a diagram for illustrating a control sequence of opening and closing the second valve and a third valve alternately;

FIG. 6 is a graph showing the relationship between the number m of times the second valve and the third valve are opened and closed and the pressure P of the hydrogen storage;

FIG. 10 is a diagram showing the open or closed state of valves involved in the hydrogen absorption-desorption cycle measurement of FIG. 8;

FIG. 14 is a diagram showing the open or closed state of the valves involved in the hydrogen absorbing characteristics measurement of FIG. 12;

FIG. 18 is a diagram showing the open or closed state of the valves involved in the hydrogen desorbing characteristics measurement of FIG. 16;

DETAILED DESCRIPTION OF EMBODIMENT

Figure 1:
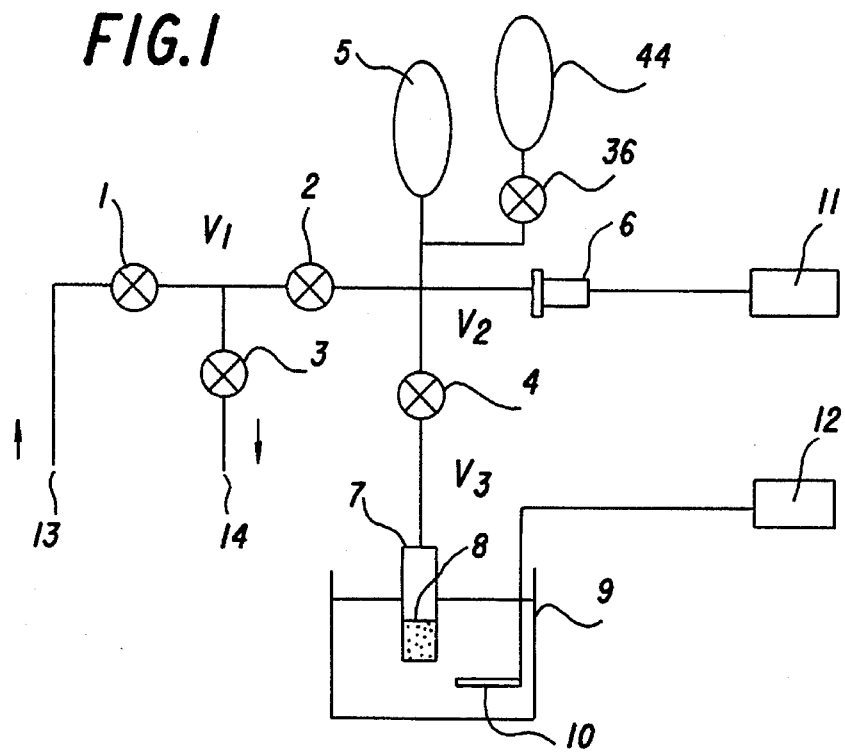
FIG. 1 is a fragmentary schematic diagram of an apparatus embodying the invention.

FIG. 1 is a fragmentary schematic diagram of an apparatus embodying the present invention.

Since a hydrogen absorbing alloy is used as the sample for the embodiment, hydrogen gas is used as the gas to be checked for characteristics, but the invention is not limited to this case. For example, the embodiment is of course usable for a substance which forms a nitride by absorbing nitrogen.

Indicated at 1 in FIG. 1 is a first valve, at 2 a second valve, at 3 a third valve, and at 4 a fourth valve. These valves are each a two-position valve having an open position and a closed position. According to the embodiment, the valve is a pneumatic valve. When the pneumatic valve is opened in response to an operating signal from outside, air flows there-into, holding the valve in the open position. The inside space of the piping surrounded by the first valve 1, second valve 2 and third valve 3 serves as a preliminary storage having a constant volume V1 which is 7 ml in the case of the embodiment.

The inside region of the piping defined by the second valve 2 and the fourth valve 4 serves as a hydrogen storage, the volume of which is expressed by V2.

The portion of the piping connecting the second valve 2 to the fourth valve 4 can be provided with a hydrogen storage container 5. When this container 5 is provided, the space volume V2 of the hydrogen storage is the sum of the inside volume of the piping and the volume of the hydrogen storage container 5. With the present embodiment, V2 is 40 ml.

A gas holder 44 can be connected to the hydrogen storage via a valve 36. The total volume of the hydrogen storage is variable by opening this valve 36. The total volume of the hydrogen storage is selectively variable over a wide range by setting the gas holder 44 at an altered volume.

The volume of the gas holder 44 is 310 ml according to the embodiment. The gas holder provided makes it possible to vary the space volume V2 of the hydrogen storage over the range of 40 to 350 ml.

Indicated at 6 is a pressure sensor for measuring the pressure of the hydrogen storage. The pressure measured by the sensor 6 is indicated by a pressure indicator 11. A sample container 7 is used for holding a hydrogen absorbing alloy as a sample 8 in the form of a powder. The amount of the alloy is about 5 g in weight. The sample container 7 comprises a closed receptacle for substantially holding the sample 8 therein, and piping for connecting the closed receptacle to the fourth valve 4. The sample container 7 has a definite volume V3, which is in the range of 20 to 30 ml.

A thermostat 9 is means for maintaining at a constant temperature the sample container 7 holding the hydrogen absorbing alloy, and contains a heat medium in the form of a 1:1 mixture of ethylene glycol and water. The temperature of the sample container 7 and the sample 8 can be varied over the range of −40° C. to less than 100° C. by using the heat medium. The temperature of the heat medium is measured by a temperature sensor 10 and indicated by a temperature indicator 12.

The first valve 1 is connected to a hydrogen supply source by a supply pipe 13. The third valve 3 is connected to a hydrogen discharge portion by a discharge pipe 14.

The piping constituting the line and the containers, etc. connected to the line are made preferably of stainless steel for the prevention of corrosion.

Figure 2:
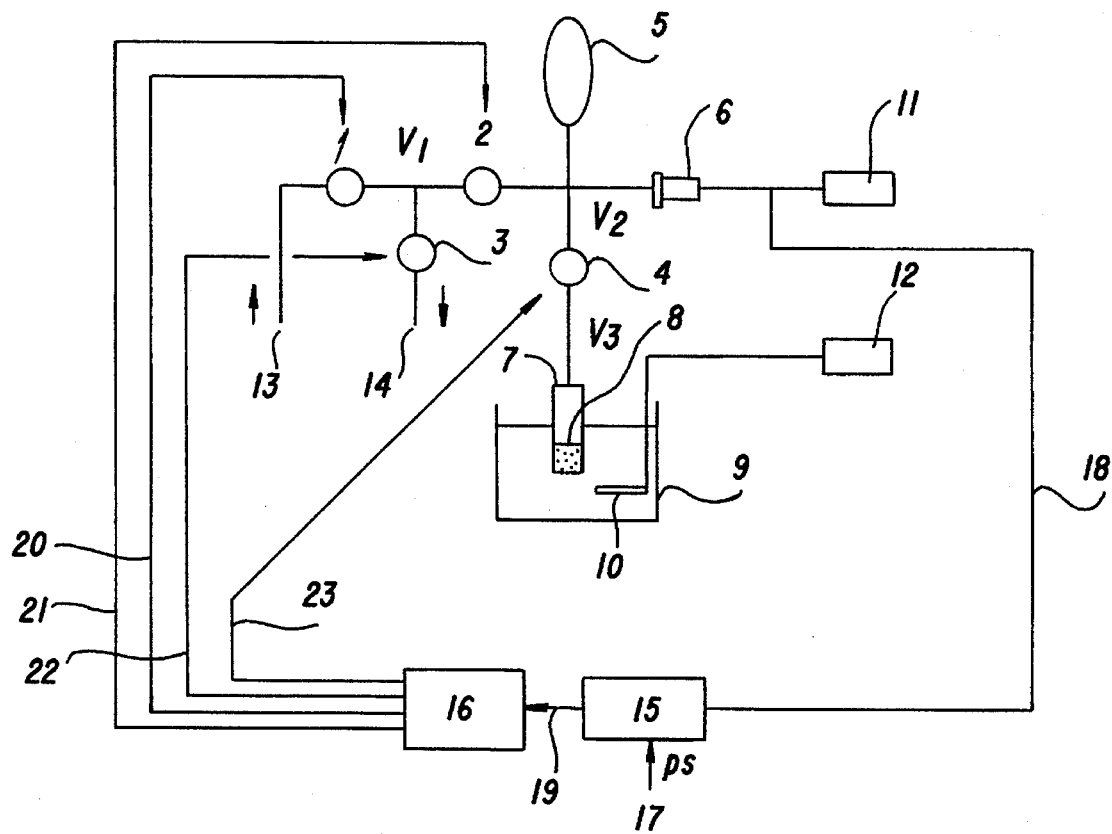
FIG. 2 is a schematic diagram of the apparatus embodying the invention.

Next, the concept of the present apparatus including the control thereof will be described with reference to FIG. 2. The pressure P measured by the pressure sensor 6 is fed to a computer 15 through a signal line 18. The computer 15 is given a set value $P^s$ 17 in advance, compares the pressure P with this value and delivers an output 19 in the form of an output signal for controlling the opening-closing operation of the valves. The output 19 is fed to valve control means 16. The valve control means 16, which is called a sequencer, feeds respective opening-closing signals to the first valve 1 through the signal line 20, to the second valve 2 through the signal line 21, to the third valve 3 through the signal line 22 and to the fourth valve 4 through the signal line 23 to open and close the first valve 1 to the fourth valve 4 according to the output 19.

Pressure Increasing Process

First, a description will be given of a pressure increasing process for causing the sample 8 to absorb hydrogen.

A control sequence of opening and closing the first valve 1 and the second valve 2 alternately will be described with reference to FIG. 3. In FIG. 3, "C" represents the closed state of the valve, and "O" represents the open state of the valve. The process includes the following steps (1) to (5). The third valve 3 remains closed in the present process.

(1) The first valve 1 is opened to supply hydrogen gas from the hydrogen supply source to the preliminary storage.

(2) The first valve 1 is closed. At this time, the pressure of the preliminary storage V1 is held at the same level as the pressure of the supply source. The pressure of the hydrogen supply source is generally reduced by a regulator.

(3) The second valve 2 is opened with the first valve 1 left closed, whereby the hydrogen gas held in the preliminary storage is supplied to the hydrogen storage.

(4) The second valve 2 is closed.

(5) The steps (1) to (4) are repeated until the pressure P of the hydrogen storage reaches the set value $P^s$.

In this way, the increase of the pressure of the hydrogen storage at least to the set value $P^s$ is recognized, whereupon the steps (1) to (4) of opening and closing the first valve 1 and the second valve 2 are terminated, followed by a measuring mode. For example, the fourth valve 4 is opened to supply the hydrogen gas to the sample 8.

With the apparatus of the invention, the first and second valves 1, 2 are opened and closed by the steps (1) to (5). FIG. 4 shows the relationship between the number m of times these valves are opened and closed and the internal pressure P of the hydrogen storage (V2 in volume). Thus, the pressure of the hydrogen storage can be increased to the set value $P^s$.

Pressure Decreasing Process

Next, a description will be given of an example of pressure decreasing process for desorbing hydrogen from the sample 8 with reference to FIGS. 5 and 6.

FIG. 5 shows a control sequence of opening and closing the second valve 2 and the third valve 3 alternately. In FIG. 5, the closed state of the valve is represented by "C", and the open state of the valve by "O". The process comprises the following steps (1) to (5). The first valve 1 remains closed during the present process.

(1) The third valve 3 is opened to discharge hydrogen gas from the preliminary storage to the hydrogen discharge portion via the discharge pipe 14. The discharge portion has a vacuum pump, which is used for evacuating the preliminary storage to a vacuum.

(2) The third valve 3 is closed. At this time, the preliminary storage V1 is maintained almost in a vacuum.

(3) The second valve 2 is opened with the third valve 3 held closed, whereby hydrogen gas held in the hydrogen storage is supplied to the preliminary storage.

(4) The second valve 2 is closed.

(5) The steps (1) to (4) are repeated until the pressure P of the hydrogen storage reaches a set value $P^s$.

In this way, the decrease of pressure of the hydrogen storage at least to the set value $P^s$ is recognized, whereupon a measuring mode follows. For example, the fourth valve 4 is opened to discharge hydrogen gas from the sample container 7.

The third valve 3 and the second valve 2 are alternately opened and closed by the steps (1) to (5). FIG. 6 shows the relationship between the number m of times these valves are opened and closed and the pressure P within the hydrogen storage (V2 in volume). Thus, the pressure of the hydrogen storage can be decreased stepwise to the set value $P^s$.

Entire Construction of Apparatus of the Invention

Figure 7:
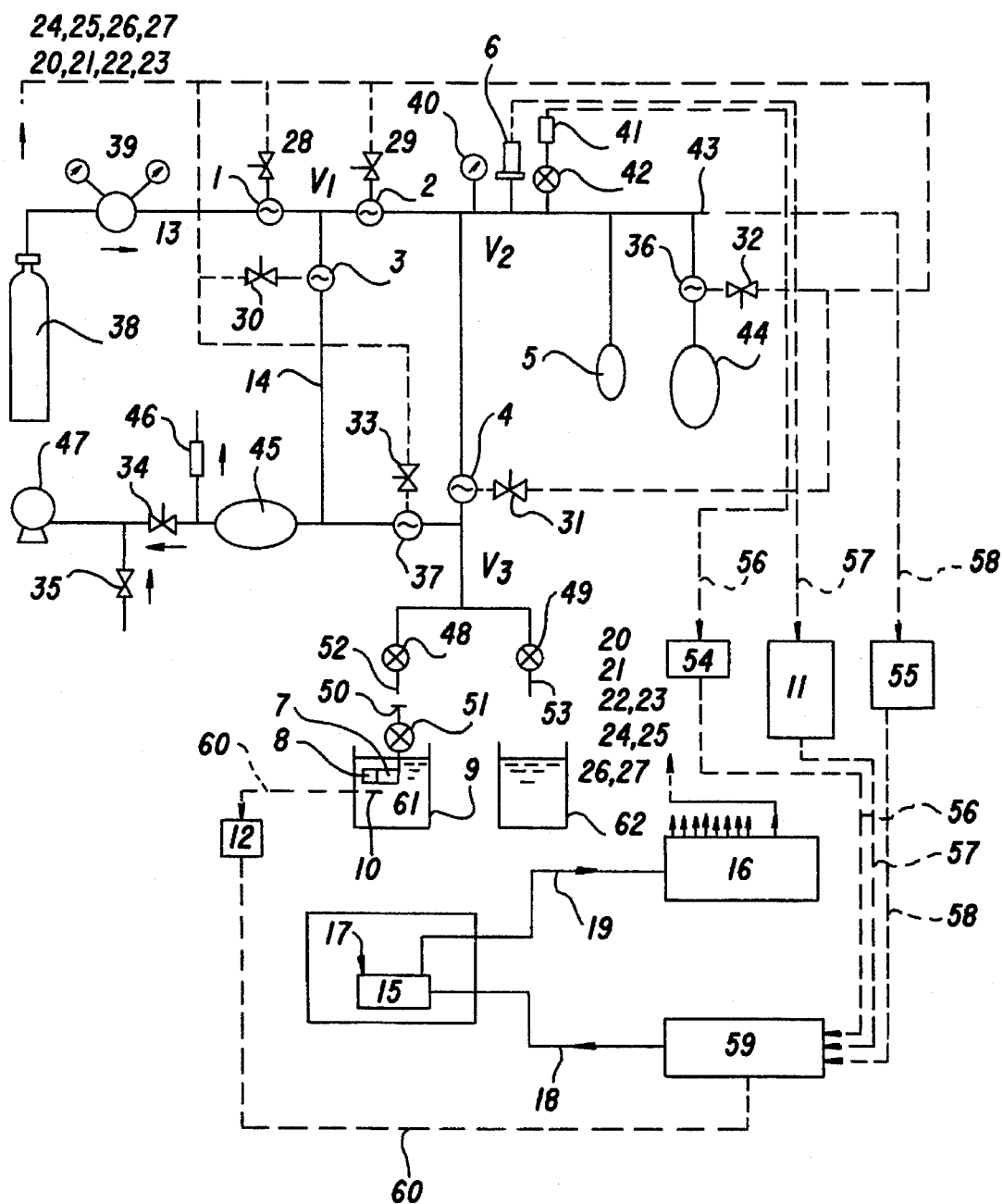
FIG. 7 is a diagram showing the entire construction of the apparatus embodying the invention.

FIG. 7 is a diagram showing the entire construction of the apparatus according to the embodiment. The portions already described with reference to FIGS. 1 to 6 will not be described again.

The signal line 20 extending from the valve control means 16 is connected to an electromagnetic valve 28, which is opened and closed in response to an opening-closing signal from the valve control means 16. When the valve 28 is opened, compressed air is supplied to the first valve 1, holding the first valve 1 in the open state. Conversely when the valve 28 is closed, the supply of compressed air is shut off to close the first valve 1.

Similarly, the signal line 21 is connected to an electromagnetic valve 29, the signal line 22 to an electromagnetic valve 30, the signal line 23 to an electromagnetic valve 31, a signal line 24 to an electromagnetic valve 32, and a signal line 25 to an electromagnetic valve 33. The valve 29 is connected to the second valve 2, the valve 30 to the third valve 3, the valve 31 to the fourth valve 4, the valve 32 to the valve 36, and the valve 33 to a valve 37. Opening and closing the respective electromagnetic valves open and close the corresponding valves, respectively, in the same manner as described above.

Especially signal lines 26 and 27 are connected to electromagnetic valves 34 and 35, respectively. The valve 34, when opened, aspirates hydrogen gas remaining at various portions. The valve 35 is a leak valve. When opened, the electromagnetic valve 35 prevents reverse flow of oil contained in the vacuum pump 47 when the pump 47 is stopped.

In the above apparatus, hydrogen gas is supplied from a hydrogen gas cylinder 38. When filled up, the cylinder 38 has a gas pressure of 12 to 15 MPa. The hydrogen pressure of the cylinder is reduced to a predetermined level by a regulator 39. The hydrogen gas of reduced pressure is supplied to the first valve 1 through the supply pipe 13. The pressure is reduced usually to a value of about 5 to about 6 MPa.

The pressure of the hydrogen storage container 5 provided for the hydrogen storage is indicated by a pressure gauge. The pressure is measured also by the pressure sensor 6. A vacuum gauge 41 connected to the hydrogen storage container 5 via a valve 42 measures the degree of vacuum in the container 5 and the sample container 7 when these containers are evacuated. Further connected to the hydrogen storage container 5 is a temperature sensor 43 for measuring the temperature of the hydrogen gas in the hydrogen storage.

A vacuum discharge portion will be described next. The vacuum discharge portion comprises the above-mentioned electromagnetic valves 34, 35 and vacuum pump 47, and further a buffer tank 45 and a relief valve 46. The vacuum discharge portion is connected by the discharge pipe 14 to the third valve 3 and the valve 37. During evacuation, the gas is temporarily admitted into the buffer tank 45, thereby reduced in pressure moderately and released through the relief valve 46 for a further pressure reduction. In the case where the gas released is hydrogen or like combustible gas, it is desired to collect the gas. The internal pressure of the buffer tank 45 is reduced approximately to atmospheric pressure, and the electromagnetic valve 34 is opened to effect evacuation without overloading the vacuum pump 47.

Next, the sample container 7 will be described. The sample container 7 comprises a sample holder 61, the hydrogen absorbing alloy 8 as a sample, the thermostat 9, the temperature sensor 10 for the thermostat, a first manual valve 48, a second manual valve 49 and a holder opening-closing valve 51. The sample holder 61 is packed with the alloy 8 in the form of a powder. The sample holder 61 is connected to the first manual valve 48 via the holder opening-closing valve 51. Provided between the valve 51 and the valve 48 are a sample-side connector 50 and a first manual valve-side connector 52. The sample-side connector 50 can be separated from the valve-side connector 52 to remove the sample holder 61. In this state, the second valve 49 is closed.

The sample holder 61 is immersed in the thermostat 9. When there arises a need for measuring temperatures in excess of the temperature range of the thermostat 9, an auxiliary thermostat 62 is prepared. The auxiliary thermostat 62 contains a heat medium comprising silicone oil. This heat medium is variable in temperature over the range of about 50° C. to about 200° C. The temperature of the medium is measured also by the temperature sensor 10 as shifted. For measurement with use of the auxiliary thermostat 62, the sample-side connector 50 is connected to a second valve-side connector 53. In this case, the first manual valve 48 is held closed.

The foregoing procedure affords analog measurements, which are converted into digital data by a data logger 59. Stated more specifically, the pressure sensor 6 produces a gas pressure signal, which is then fed to the pressure indicator 11 for indication via a signal line 57 and is further fed to the data logger 59. The vacuum gauge 41 feeds a vacuum degree signal to a vacuum degree indicator 54 via a signal line 56 for indication, and the signal is fed also to the data logger 59. Additionally, the temperature sensor 43 produces a gas temperature signal, which is fed to a temperature indicator 55 via a signal line 58 for indication and is further fed also to the data logger 59. The thermostat temperature sensor 10 produces a thermostat temperature signal, which is fed to the thermostat temperature indicator 12 through a signal line 60 for indication and is further fed similarly to the data logger 59.

The items of digital data as converted by the data logger 59 are given to the computer 15 through the signal line 18, and are preserved when so desired.

Hydrogen Absorption-Desorption Cycle Measurement

Figure 8:
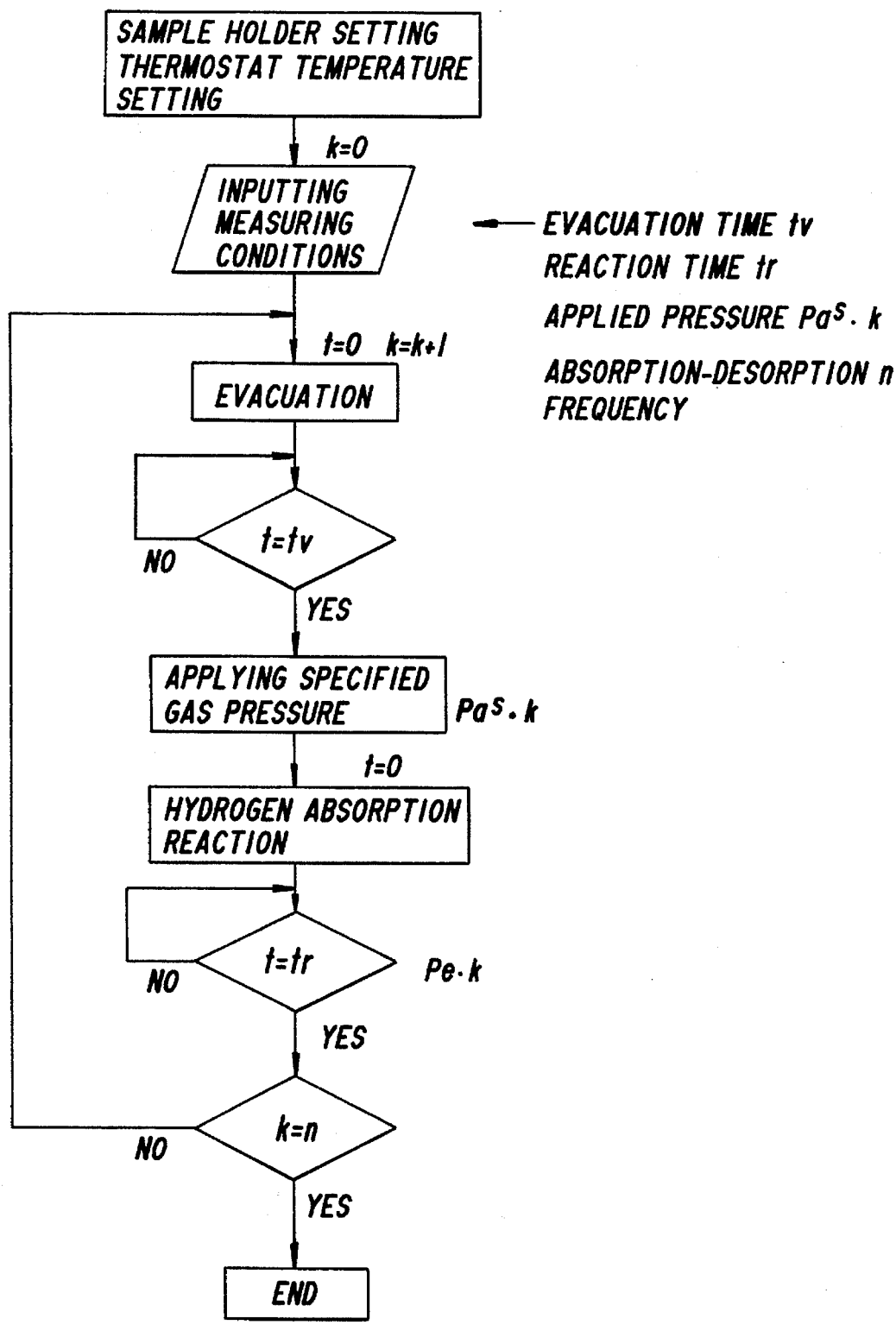
FIG. 8 is a flow chart of hydrogen absorption-desorption cycle measurement conducted with use of the apparatus of the invention.

The apparatus of the present invention is used for checking hydrogen absorbing alloys for cycle life. FIG. 8 is a flow chart of hydrogen absorption-desorption cycle measurement, which will be described below.

(1) The sample holder 61 is connected to the main body of the apparatus, and the thermostat is set to a desired temperature. Absorption-desorption frequency k is set at 0.

(2) Measuring conditions are input to the computer 15. More Specifically, evacuation time is set at tw, reaction time at tr, set value of the pressure to be applied at $Pa^s \cdot k$, and absorption-desorption frequency at n as the measuring conditions. These conditions are variable as desired in the subsequent steps.

(3) Time t is set at 0, and absorption-desorption frequency k is set at k+1.

(4) The sample holder 61 is evacuated until time t becomes tv.

(5) Hydrogen gas of specified gas pressure $Pa^s \cdot k$ is introduced into the hydrogen storage. The specified gas pressure $Pa^s \cdot k$ is the set pressure to be applied in the absorption-desorption cycle for the kth absorption and desorption.

(6) Time t is set at 0.

(7) Effect a hydrogen absorption reaction until time t becomes tr. When t=tr, the pressure P is measured to obtain $Pe \cdot k = P$.

(8) When the absorption-desorption frequency k is n, the cycle measurement is terminated. If otherwise, the steps (3) to (7) are repeated.

Figure 9:
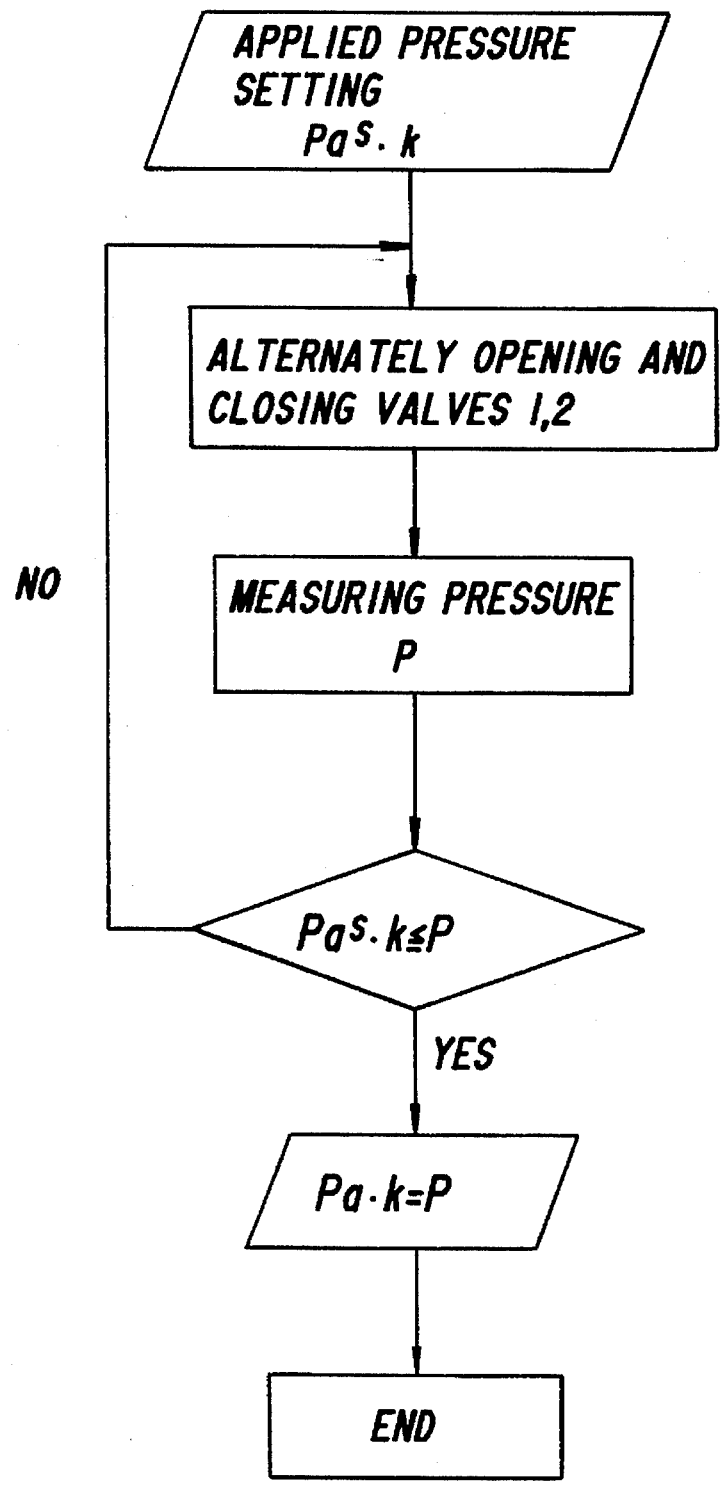
FIG. 9 is a flow chart of applying a predetermined pressure in the hydrogen absorption-desorption cycle measurement of FIG. 8.

The hydrogen absorption-desorption cycle measurement is completed by the foregoing steps (1) to (8). The step (5) in particular will be described in detail with reference to FIG. 9, a flow chart of applying the specified pressure in the hydrogen absorption-desorption cycle measurement. The step (5) includes the following steps (5)-1 to (5)-4.

(5)-1: The pressure $Pa^s \cdot k$ to be applied is automatically set at a value obtained by adding a pressure difference $\Delta P$ to be applied, to absorption equilibrium pressure $Pe \cdot k-1$ in the immediately preceding absorption reaction step (k-1).

(5)-2: The first valve 1 and the second valve 2 are alternately opened and closed by the pressure increasing process previously described to introduce hydrogen gas into the hydrogen storage.

(5)-3: The hydrogen gas pressure P of the hydrogen storage is measured.

(5)-4: When the gas pressure P increases to at least the applied pressure set value $Pa^s \cdot k$, $Pa \cdot k = P$ to terminate the specified gas pressure application step. While the set value $Pa^s \cdot k$ is made approximate to $Pa \cdot k$, the difference between $Pa^s \cdot k$ and $Pa \cdot k$ can be diminished by decreasing the space volume of the preliminary storage. If the hydrogen gas pressure P is below the set value $Pa^s \cdot k$, the foregoing steps (5)-2 to (5)-4 are repeated.

The step of applying the specified gas pressure is completed by the steps (5)-1 to (5)-4.

FIG. 10 shows the open or closed state of the valves in the hydrogen absorption-desorption cycle measurement conducted by the steps (1) to (8). In FIG. 10, the closed state of the valve is represented by "C", and the open state of the valve by "O", and "C←→O" or "O←→C" means repetition of the open state and the closed state.

Figure 11:
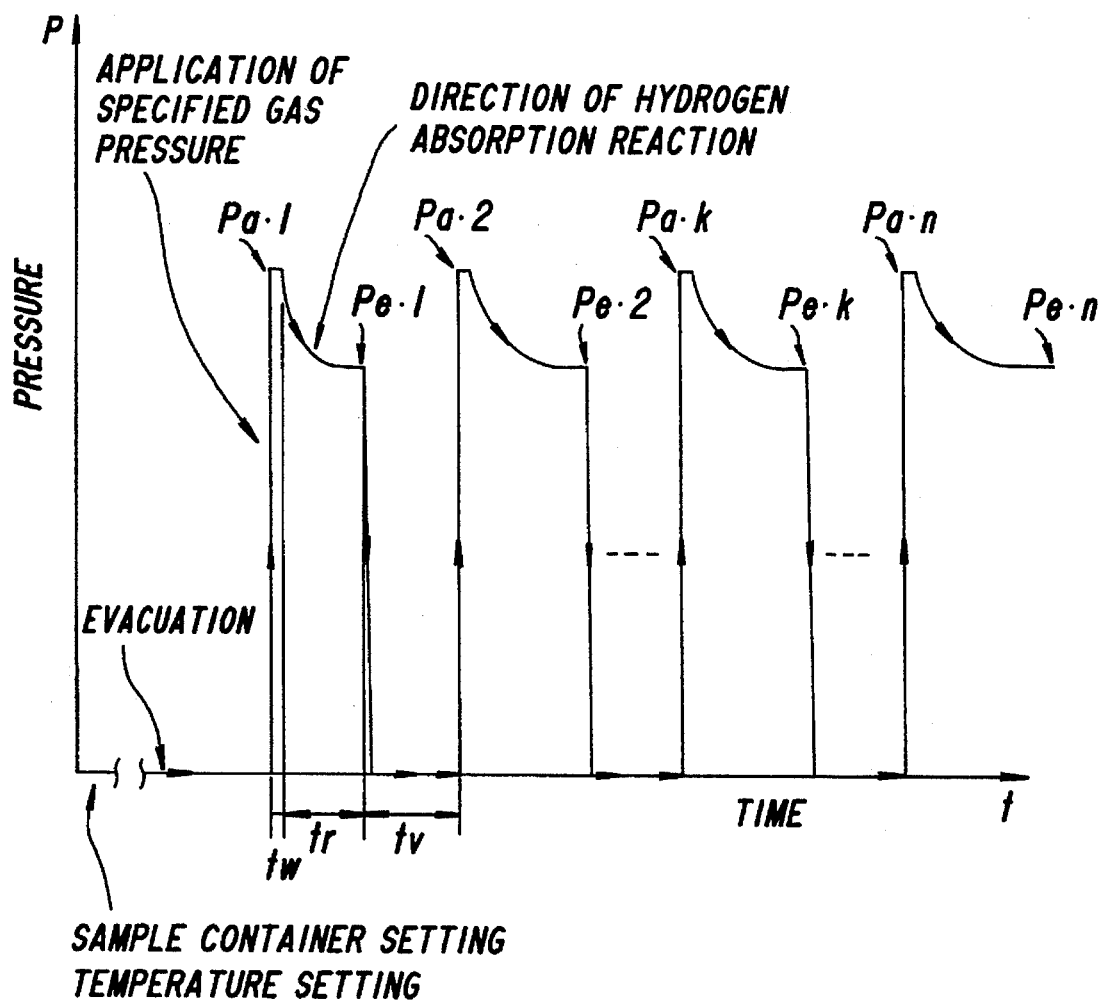
FIG. 11 is a diagram showing pressure variations with time as involved in the hydrogen absorption-desorption cycle measurement of FIG. 8.

FIG. 11 shows pressure variations with time as involved in the hydrogen absorption-desorption cycle measurement. In FIG. 11, tw is a waiting time required for the hydrogen gas temperature, raised by an adiabatic compression effect after the application of specified gas pressure, to be brought to a steady state. The value is set in the computer 15 in advance.

Measurement of Hydrogen Absorbing Characteristics for PCT Characteristics Curve

The apparatus of the invention is used for preparing PCT characteristics curves.

Figure 12:
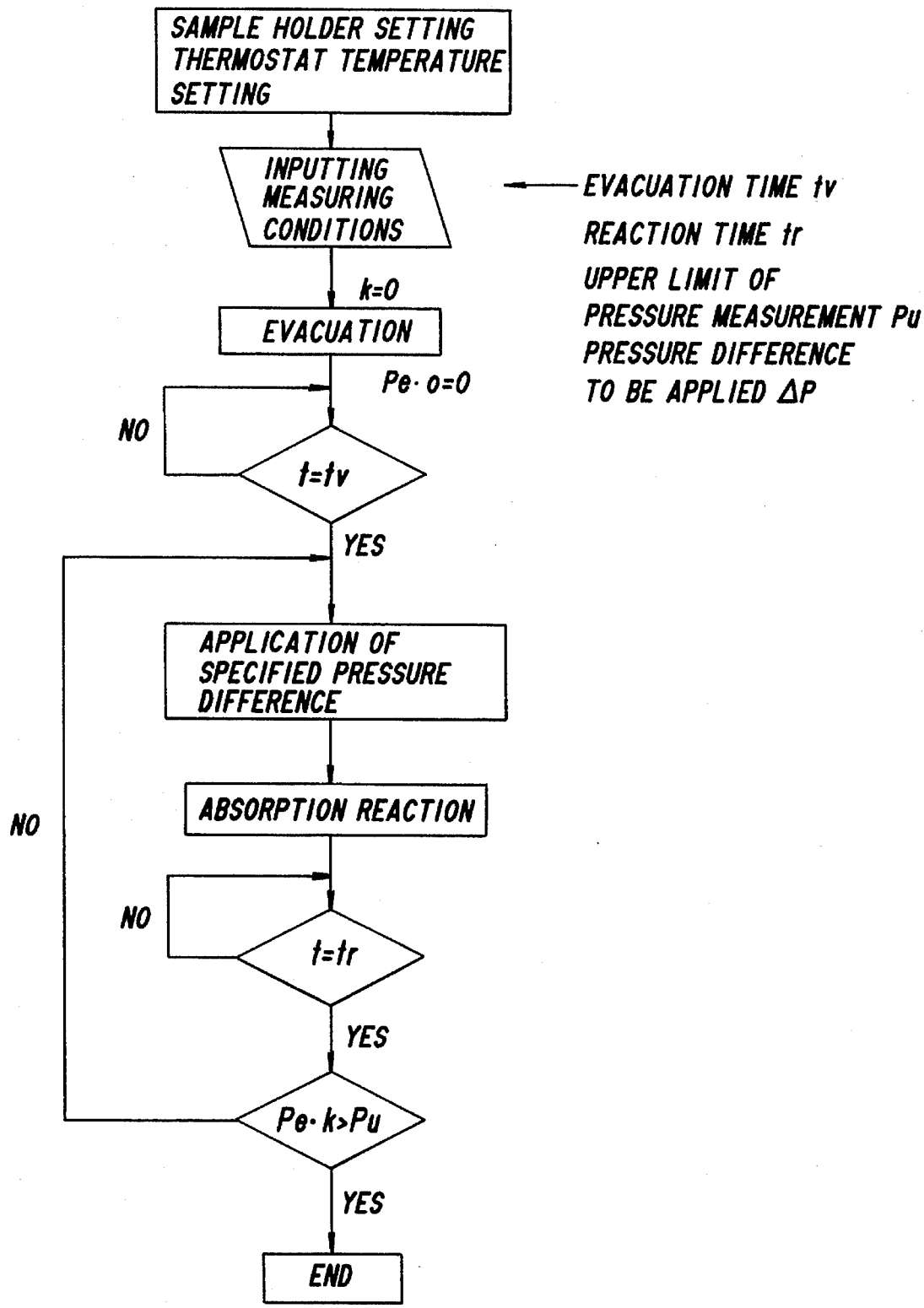
FIG. 12 is a flow chart of measuring hydrogen absorbing characteristics for preparing a PCT diagram with use of the apparatus of the invention.

FIG. 12 is a flow chart of measuring hydrogen absorbing characteristics. The measuring operation will be described below.

(1) The sample holder 61 is connected to the main body of the apparatus, and the thermostat 9 is set at a desired temperature. The number of steps, k, of the absorption reaction is set at 0.

(2) Measuring conditions are input to the computer 15. More specifically, evacuation time is set at tv, reaction time at tr, the upper limit of the pressure to be measured at Pu, and pressure difference between applied pressures at ΔP as the measuring conditions. These conditions are variable as desired in the subsequent steps.

(3) Time t is set at 0.

(4) The sample holder 61 is evacuated until time t becomes tv.

(5) Hydrogen gas of specified gas pressure $Pa^s \cdot k$ is introduced into the hydrogen storage. The specified gas pressure $Pa^s \cdot k$ is the set pressure to be applied for the absorption reaction of the kth step.

(6) Time t is set at 0.

(7) Effect the hydrogen absorption reaction until time t becomes tr. When t=tr, the pressure P is measured to obtain $Pe \cdot k = P$.

(8) When the equilibrium hydrogen gas pressure $Pe \cdot k$ in the kth absorption reaction step is greater than Pu, the PCT characteristics curve measurement in the hydrogen absorption process is terminated. If $Pe \cdot k$ is not greater than Pu, the foregoing steps (5) to (7) are repeated.

Figure 13:
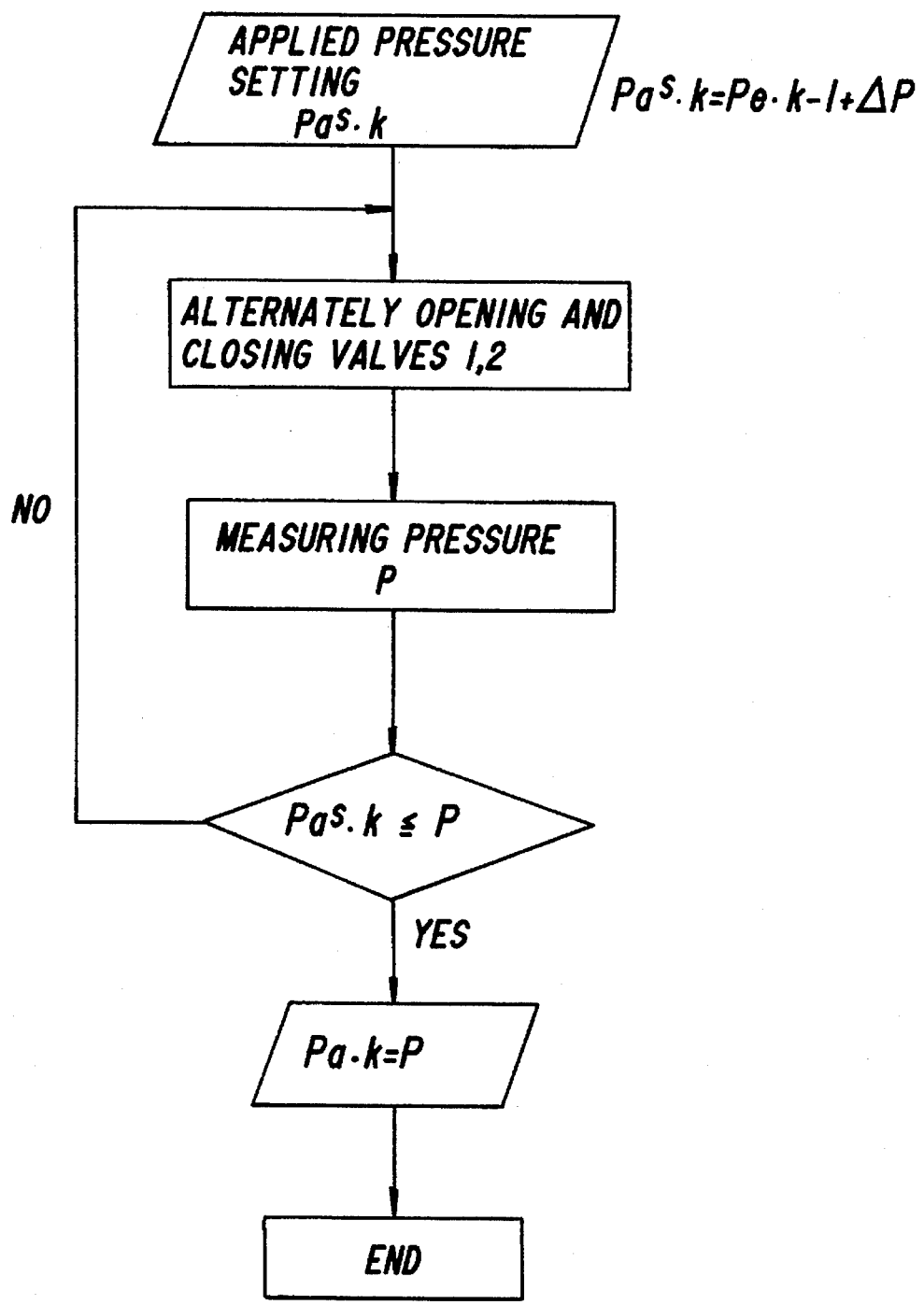
FIG. 13 is a flow chart of appying a predetermined pressure in the hydrogen absorbing characteristics measurement of FIG. 12.

The measurement of hydrogen absorption characteristics for preparing the PCT characteristics curve is completed by the steps (1) to (8). The step (5) in particular comprises the following steps (5)-1 to (5)-4 when described in greater detail with reference to FIG. 13, a flow chart of applying the specified pressure.

(5)-1: The pressure $Pa^s \cdot k$ to be applied is automatically set at a value obtained by adding a pressure difference ΔP to be applied, to absorption equilibrium pressure $Pe \cdot k-1$ in the immediately preceding absorption reaction step (k-1).

(5)-2: The first valve 1 and the second valve 2 are alternately opened and closed by the pressure increasing process previously described to introduce hydrogen gas into the hydrogen storage.

(5)-3: The hydrogen gas pressure P of the hydrogen storage is measured.

(5)-4: When the gas pressure P increases to at least the applied pressure set value $Pa^s \cdot k$, $Pa \cdot k = P$ to terminate the specified gas pressure application step. If the hydrogen gas pressure P is below the set value $Pa^s \cdot k$, the foregoing steps (5)-2 to (5)-4 are repeated.

The step of applying the specified gas pressure is completed by the steps (5)-1 to (5)-4.

FIG. 14 shows the open or closed state of the valves in the hydrogen absorbing characteristics measurement conducted by the steps (1) to (8). In FIG. 14, the closed state of the valve is represented by "C", and the open state of the valve by "O", and "C←→O" or "O←→C" means repetition of the open state and the closed state.

Figure 15:
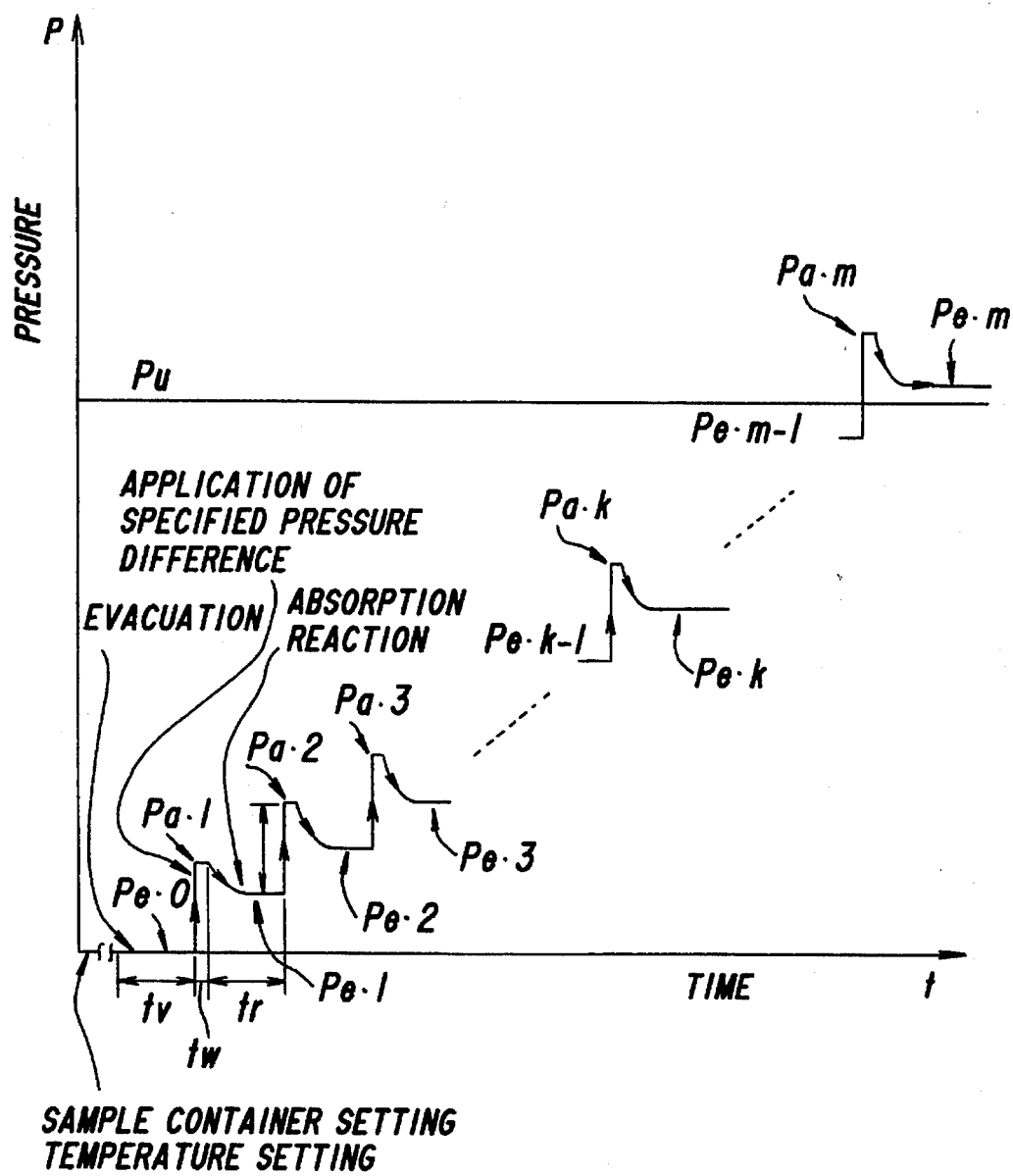
FIG. 15 is a diagram showing pressure variations with time as involved in the hydrogen absorbing characteristics measurement of FIG. 12.

FIG. 15 shows pressure variations with time as involved in the hydrogen absorbing characteristics measurement for the PCT characteristics curve. In FIG. 15, tw is a waiting time required for the hydrogen gas temperature, raised by an adiabatic compression effect after the application of specified gas pressure, to be brought to a steady state. The value is set in the computer 15 in advance.

Measurement of Hydrogen Desorbing Characteristics for PCT Characteristics Cuve

Figure 16:
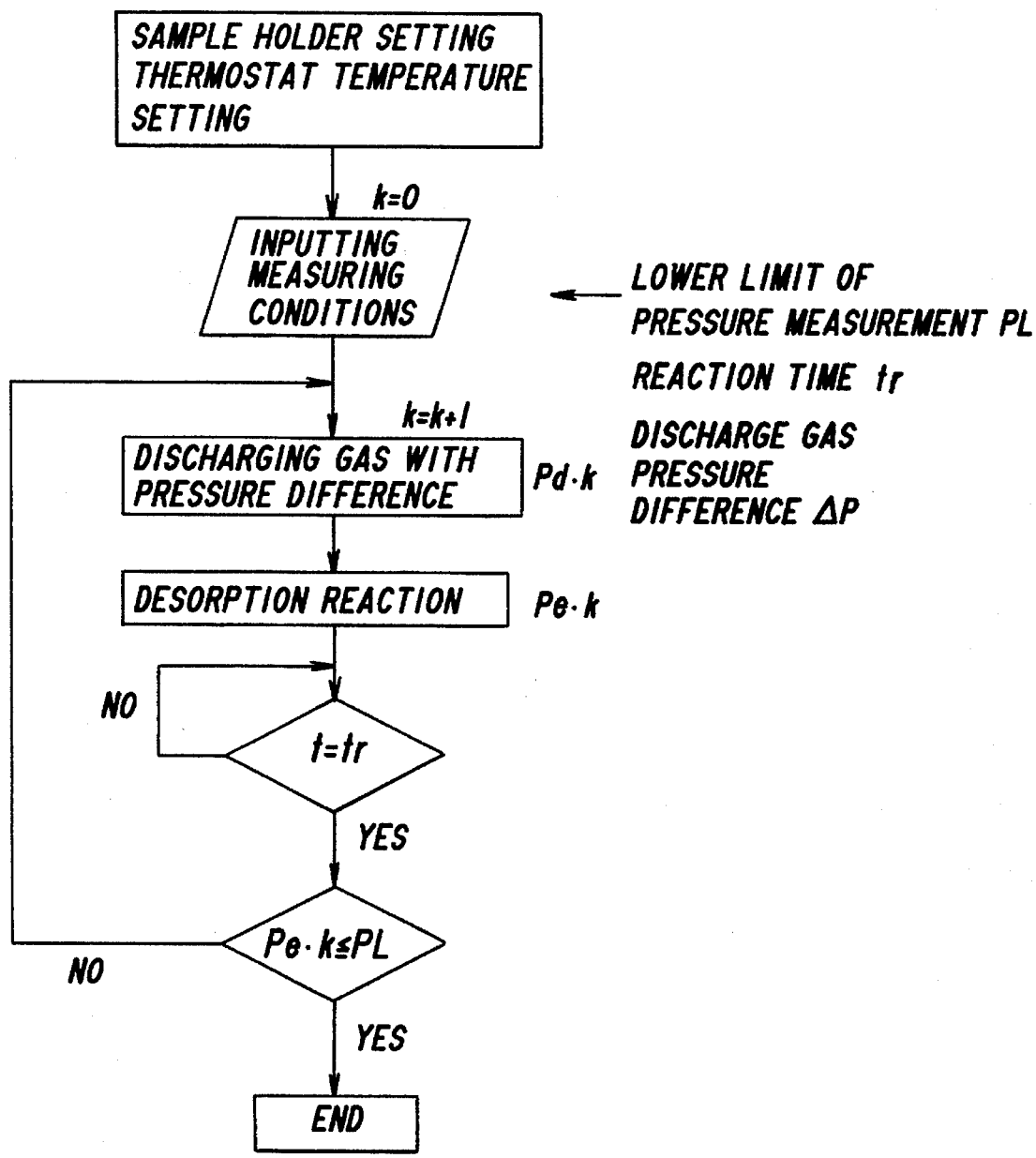
FIG. 16 is a flow chart of measuring hydrogen desorbing characteristics for preparing a PCT diagram with use of the apparatus of the invention.

FIG. 16 is a flow chart of measuring hydrogen desorbing characteristics for the PCT characteristics curve. The measuring operation will be described below.

(1) The sample holder 61 is connected to the main body of the apparatus, and the thermostat 9 is set at a desired temperature. The number k of desorption reaction steps is set at 0.

(2) Measuring conditions are input to the computer 15. More specifically, reaction time is set at tr, the lower limit of the pressure to be measured at $P_L$, and difference of the pressure of discharge gas at ΔP as the measuring conditions. These conditions are variable as desired in the subsequent steps.

(3) Hydrogen gas of specified pressure $Pd \cdot k$ is discharged from the hydrogen storage. The specified gas pressure $Pd \cdot k$ is the desporption pressure of the kth desorption reaction step.

(4) Time t is set at 0.

(5) Effect the hydrogen desorption reaction until time t becomes tr. When t=tr, the pressure P is measured to obtain $Pe \cdot k = P$.

(6) When the equilibrium hydrogen gas pressure $Pe \cdot k$ in the kth desorption reaction step is smaller than or equal to $P_L$, the PCT characteristics curve measurement in the hydrogen desorption process is terminated. If $Pe \cdot k$ is greater than $P_L$, the above steps (3) to (6) are repeated.

Figure 17:
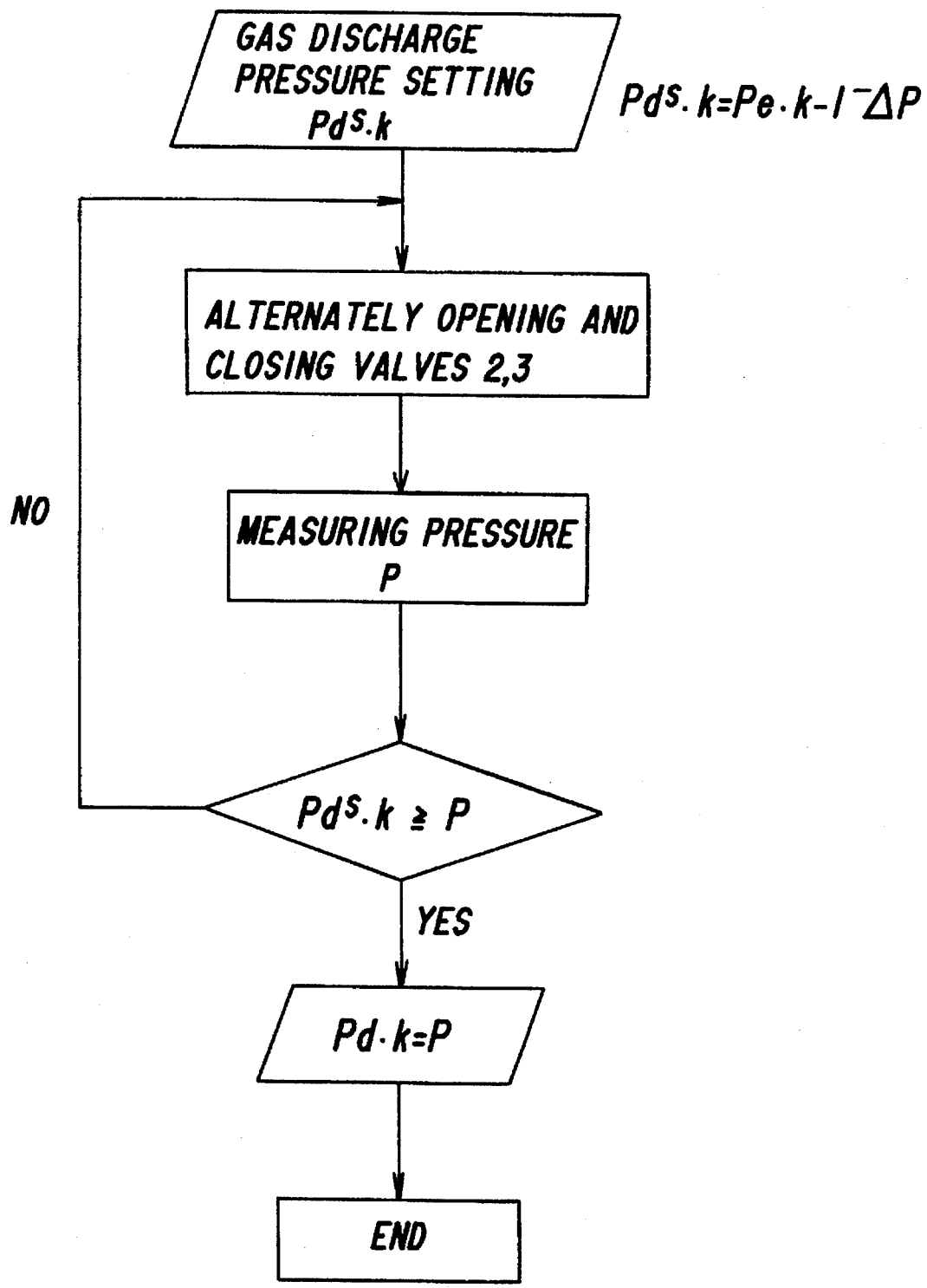
FIG. 17 is a flow chart of applying a predetermined pressure in the hydrogen desorbing characteristics measurement of FIG. 16.

The measurement of hydrogen desorbtion characteristics for preparing the PCT characteristics curve is completed by the steps (1) to (6). The step (3) in particular comprises the following steps (3)-1 to (3)-4 when described in greater detail with reference to the flow chart of FIG. 17.

(3)-1: The discharge gas pressure $Pd^s \cdot k$ is automatically set at a value obtained by subtracting the difference ΔP of discharge gas pressure from the desorption equilibrium pressure $Pe \cdot k-1$ immediately preceding desorption reaction step (1—1). When $Pe \cdot k-1 - ΔP$ is negative, Pd$^s$·k is set at 0. The discharge gas pressure Pd$^s$·k is that set for the kth desorption reaction step.

(3)-2: The second valve 2 and the third valve 3 are alternately opened and closed by the pressure decreasing process already described to discharge hydrogen gas from the hydrogen storage.

(3)-3: The hydrogen gas pressure P of the hydrogen storage is measured.

(3)-4: When the hydrogen gas pressure P decreases to not higher than the discharge gas pressure Pd$^s$·k, Pd·k=P to terminate the step of discharging the gas of specified pressure. When the hydrogen gas pressure P is higher than the discharge gas pressure Pd$^s$·k, the above steps (3)-2 to (3)-4 are repeated.

The gas discharge step is completed by the steps (3)-1 to (3)-4.

FIG. 18 shows the open or closed state of the valves in the hydrogen desorbing characteristics measurement conducted by the steps (1) to (6). In FIG. 18, the closed state of the valve is represented by "C", and the open state of the valve by "O", and "C←→O" or "O←→C" means repetition of the open state and the closed state.

Figure 19:
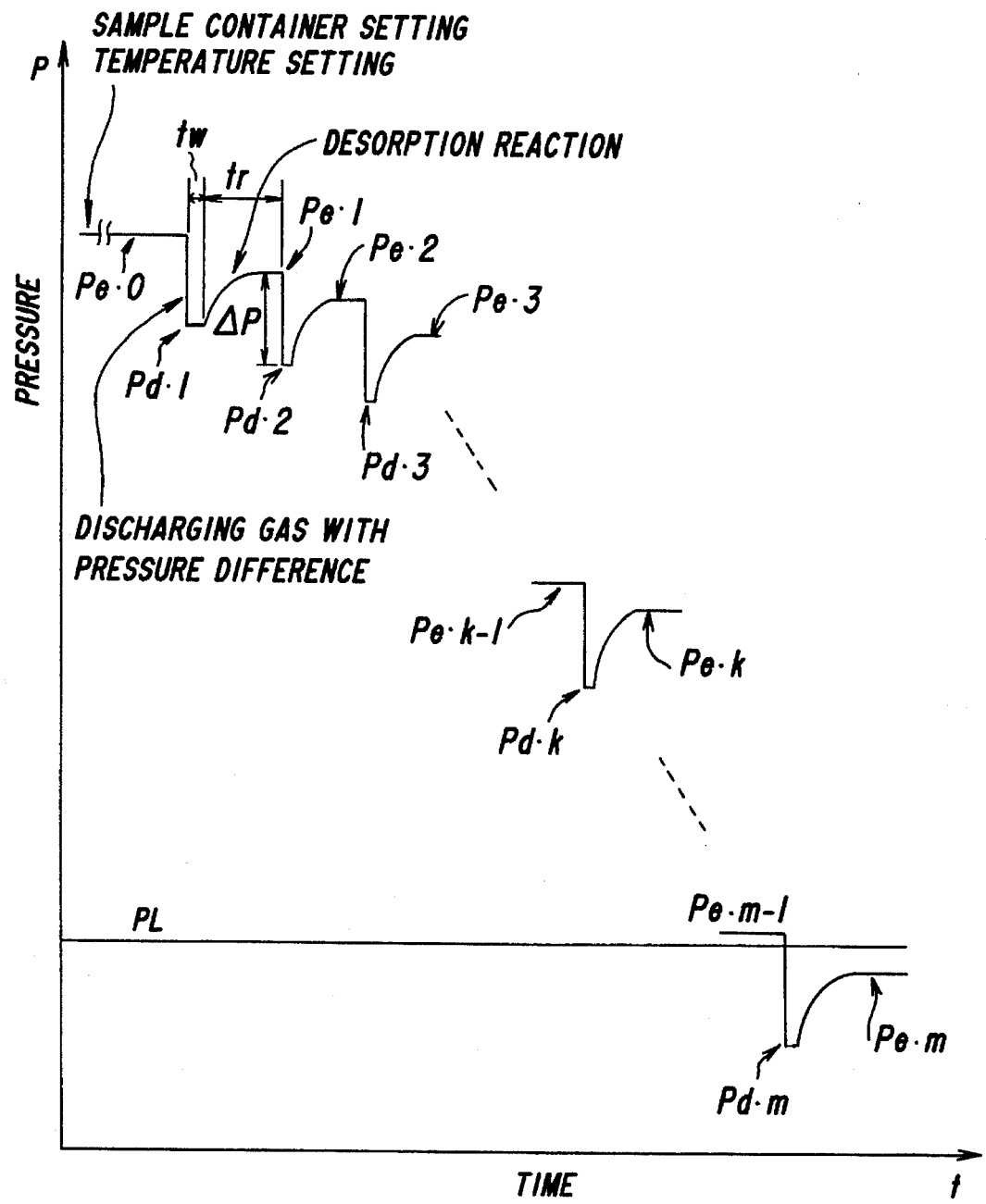
FIG. 19 is a diagram showing pressure variations with time as involved in the hydrogen desorbing characteristics measurement of FIG. 16.
Figure 20:
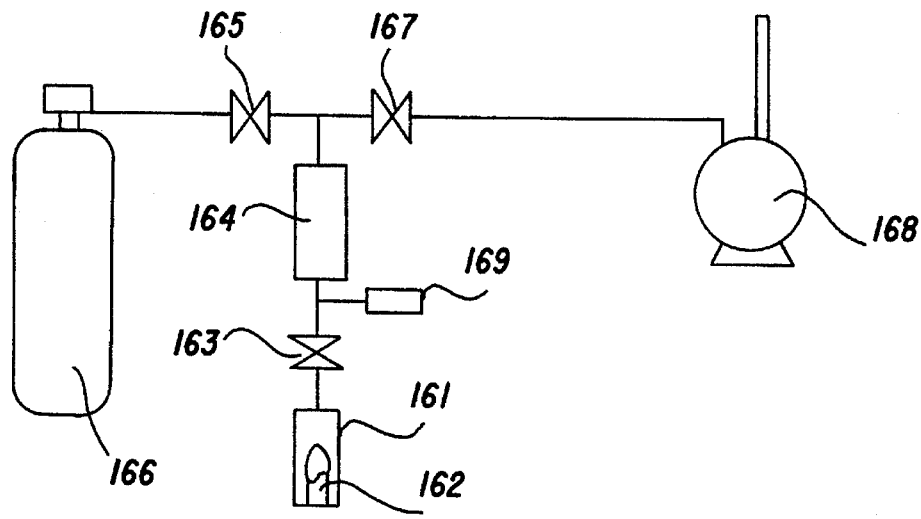
FIG. 20 is a fragmentary schematic diagram of a conventional measuring device.
Figure 21:
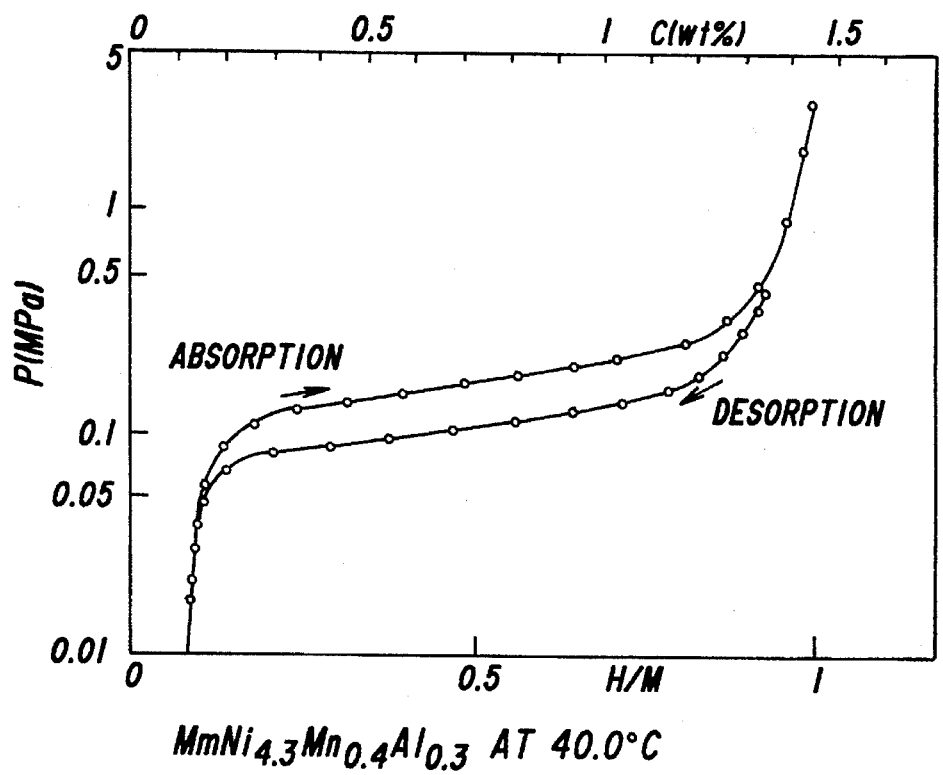
FIG. 21 is an example of PCT diagram.
Figure 22:
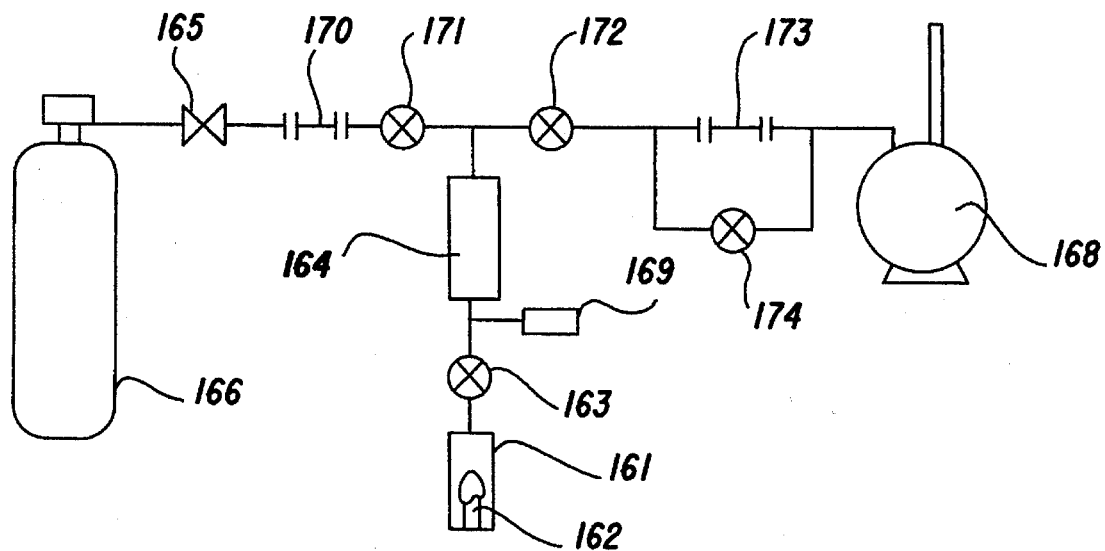
FIG. 22 is a fragmentary schematic diagram of a conventional automatic measuring device.

FIG. 19 shows pressure variations with time as involved in the hydrogen desorbing characteristics measurement for the PCT characteristics curve. In FIG. 19, tw is a waiting time required for the hydrogen gas temperature, lowered by an adiabatic expansion effect after the removal of specified gas pressure, to be brought to a steady state. The value is set in the computer 15 in advance.

The present invention provides an apparatus for measuring the characteristics, for example, of a hydrogen absorbing alloy by causing the alloy to absorb or desorb hydrogen gas, the apparatus being repeatedly usable with high stability over a prolonged period of time.

Further the present invention makes it possible to automatically control such characteristics measuring apparatus while assuring the apparatus of high measuring accuracy.

With the apparatus of the invention, a reduction in the space volume V1 of the preliminary storage decreases the amount of gas to be supplied to the gas storage V2 at a time or to be discharged from the gas storage V2 at a time. This diminishes the deviation from the set value to an almost negligible extent. Alternatively, the pressure to be applied from the hydrogen supply source is adjusted in accordance with the level of set pressure to decrease the amount of gas to be supplied to the gas storage by one valve opening-closing operation, whereby the deviation from the set value can be diminished.

Although the present invention has been described with reference to an embodiment, the invention is in no way limited to the embodiment but can be practiced as suitably modified within the scope of the invention.

What is claimed is:

1. An apparatus for measuring the gas absorbing and/or desorbing characteristics of a substance having a property to absorb a gas, the apparatus having a sample container for containing the substance, a gas storage connected to the sample container for storing the gas until a predetermined pressure is reached, and a gas supply source for supplying the gas to the gas storage, the apparatus further comprising:

a first valve provided on a line connecting the gas supply source to the gas storage, a second valve provided on a line between the first valve and the gas storage, a third valve provided on a gas discharge line connected to the line between the first valve and the second valve, the first, second and third valves being each a two-position valve having an open position and closed position, the valves defining a region thereby surrounded and serving as a preliminary storage for temporarily holding the gas when the gas is supplied or discharged, and valve control means for controlling opening and closing of the valves, the first valve and the second valve alternately opened and closed under the control of the valve control means to thereby intermittently supply the gas from the gas storage and pressurize the gas storage of pressure stepwise until the predetermined pressure is reached.

2. An apparatus as defined in claim 1 wherein the gas storage is provided with a gas holder for adjusting the amount of gas to be stored in the gas storage.

3. An apparatus as defined in claim 1 wherein valve control means is provided for controlling opening and closing of the valves, and the second valve and the third valve are alternately opened and closed under the control of the valve control means to thereby intermittently discharge the gas from the gas storage and relieve the gas storage of pressure stepwise until the predetermined pressure is reached.

4. An apparatus as defined in claim 1 wherein the substance is a hydrogen absorbing alloy, and the gas is hydrogen.

5. An apparatus for measuring the gas absorbing and/or desorbing characteristics of a substance having a property to absorb a gas, the apparatus having a sample container for containing the substance, a gas storage connected to the sample container for storing the gas until a predetermined pressure is reached, and a gas supply source for supplying the gas to the gas storage, the apparatus further comprising:

a first valve provided on a line connecting the gas supply source to the gas storage, a second valve provided on a line between the first valve and the gas storage, a third valve provided on a gas discharge line connected to the line between the first valve and the second valve, the first, second and third valves being each a two-position valve having an open position and closed position, the valves defining a region thereby surrounded and serving as a preliminary storage for temporarily holding the gas when the gas is supplied or discharged, and valve control means for controlling opening and closing of the valves, the second valve and the third valve are alternately opened and closed under the control of the valve control means to thereby intermittently discharge the gas from the gas storage and relieve the gas storage of pressure stepwise until the predetermined pressure is reached.

6. An apparatus as defined in claim 5, wherein the gas storage is provided with a gas holder for adjusting the amount of gas to be stored in the gas storage.

7. An apparatus as defined in claim 5, wherein the substance is a hydrogen absorbing alloy, and the gas is hydrogen.

* * * * *